United States Patent [19]
Bennett

[11] Patent Number: 5,355,884
[45] Date of Patent: Oct. 18, 1994

[54] APPLANATION TONOMETER FOR MEASURING INTRAOCULAR PRESSURE

[76] Inventor: Emeric S. Bennett, 12149 Fowlers Mill Rd., Chardon, Ohio 44024

[21] Appl. No.: 969,068

[22] Filed: Oct. 30, 1992

[51] Int. Cl.$^5$ .............................................. A61B 3/16
[52] U.S. Cl. ..................................... 128/645; 128/652
[58] Field of Search ........................... 128/645–646, 128/652, 774; 73/79, 862.36, 862.47–862.48

[56] References Cited

U.S. PATENT DOCUMENTS

| | | | |
|---|---|---|---|
| 3,070,997 | 1/1963 | Papritz | 73/80 |
| 4,622,459 | 11/1986 | Bouge | 250/214 |
| 4,766,904 | 8/1988 | Kozin | 128/652 |
| 4,951,671 | 8/1990 | Coan | 128/652 |
| 4,987,898 | 1/1991 | Sones | 128/645 |
| 4,987,899 | 1/1991 | Brown | 128/645 |
| 5,012,812 | 5/1991 | Stockwell | 128/652 |
| 5,070,875 | 12/1991 | Falck et al. | 128/652 X |
| 5,165,409 | 11/1992 | Coan | 128/652 |
| 5,174,292 | 12/1992 | Kursar | 128/652 X |

Primary Examiner—Angela D. Sykes

[57] ABSTRACT

An apparatus for measuring intraocular pressure within an eye, includes a probe with a premeasured maximum contact area at its outer end, and the probe is associated with a signal source leading to a signal sensor, and the probe is further associated with a force sensor. In a first embodiment, the signal originates from a light source reflected from the corneal surface through the probe to a photosensor. The reflected light increases with increasing probe-corneal surface contact to give an output which, in conjunction with the force sensor output to a microprocessor, provides the pressure per unit of the maximum contact area of the probe; i.e., the intraocular pressure. In a second embodiment, an electronic signal from probe-corneal surface contact, measured by a voltmeter, is inversely proportional to probe-corneal surface contact. A microprocessor again computes the voltage output for the predetermined maximum corneal contact and, simultaneously, the force output to provide IOP.

11 Claims, 2 Drawing Sheets

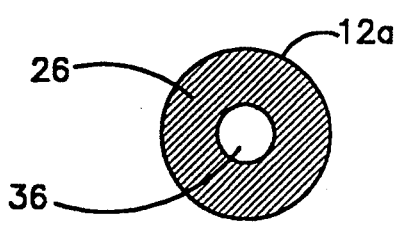
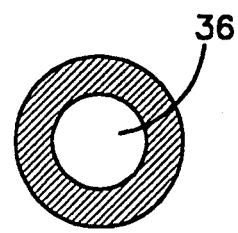
Fig.1A    Fig.1B
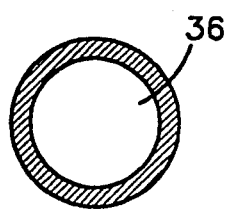
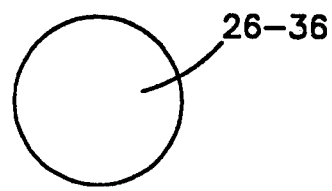
Fig.1C    Fig.1D
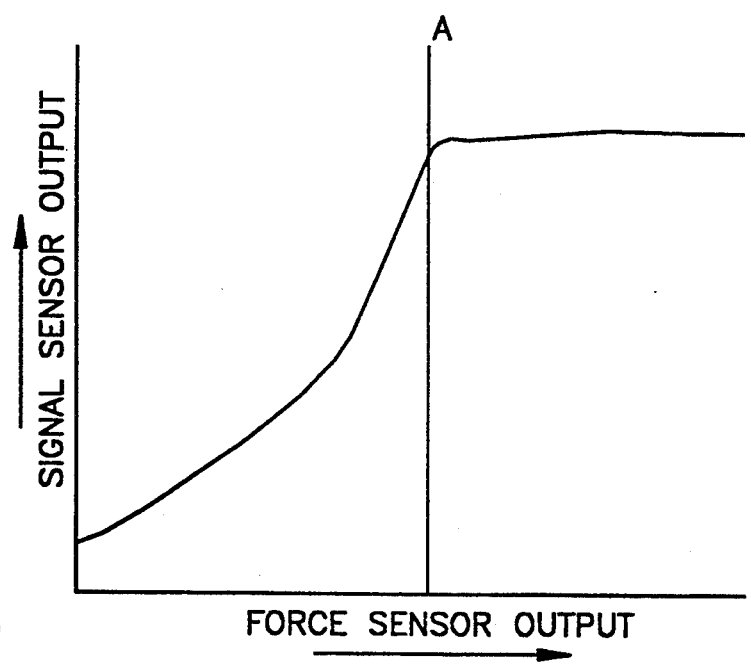
Fig.2

APPLANATION TONOMETER FOR MEASURING INTRAOCULAR PRESSURE

FIELD OF THE INVENTION

This invention pertains to an improved contact tonometer for measuring intraocular pressure of the eye. The improvements are 1) that a light or, in the alternative, an electronic signal indicates the maximum corneal surface area flattened by a probe sensorhead and at the point of a predetermined maximum contact area, calculates intraocular pressure or IOP; 2) the device obviates operator judgment; and 3) the device has no moving parts.

BACKGROUND OF THE INVENTION

Intraocular pressure (IOP) pressure is important for determining existence of disorders in the eye such as, for example, glaucoma. Such disorders bring about a change in the normal intraocular pressure in the eye. Therefore, increased intraocular pressure may signal the onset of glaucoma which can damage the ocular nerve. Measure of IOP is thus employed as an important diagnostic tool. The periodic measurement of IOP pressure, and finding the pressure to be in normal range, assists in effectively ruling out the existence of glaucoma. As such, screening for glaucoma is a major concern of public health efforts.

Testing of IOP (tonometry) has become a routine diagnostic method for detecting glaucoma. Tonometry may be defined as the noninvasive measurement of intraocular pressure. There are two tonometry methods: 1) Applanation tonometry is a process where the cornea of the eye is flattened or applanated and pressure to achieve applanation is measured per corneal area applanated; and 2) Indentation tonometry wherein the cornea is indented with a shape other than a flat surface.

Applanation by pressing the tonometer against an exterior (corneal) surface of the eye results in a flattening to a given and certain area of measurement surface of the eye and then determining the amount of force required to produce the flattening or indentation. Intraocular pressure is determined at a point when a known pressure is applied and a known applanation area is attained.

Indentation tonometry is generally accomplished by non-contact (puff) tonometers. Such non-contact tonometers use a puff of air to flatten a circular area of the cornea, whereby intraocular pressure can be measured without physical contact between the tonometer element and the eye. The pressure is derived from the force of the airstream against the eye at the instant of corneal indentation. Non-contact tonometers avoid the necessity of anesthetizing the patient's cornea. But these puff tonometers are relatively expensive; they lack accuracy and are highly dependent on operator skill. They are unreliable in the presence of corneal disease or irregular corneal surface. Therefore, they are generally used only as screening devices and are not relied upon for accurate IOP measurements.

The applanation tonometry devices presently in use for measuring intraocular pressure (contact tonometers) are placed upon, and then pressed against, the cornea of the eye. The area of tonometer contacting the surface of the eye increases as the force applied increases, because the eye deforms under the pressure of the tonometer. The pushing force divided by the contact area give a pressure, (dynes per square millimeter for example), which equals the pressure in the eye. This relationship exists because of the characteristics of the eye: mainly, the fact that it is essentially an incompressible fluid contained within an elastic membrane.

Since the pressure measurement cannot be made unless the contact area is known, prior art devices pressed the tonometer onto the eye until the entire end of the tonometer was in contact with the eye. When the operator determined the tonometer-eye contact was complete, then the force scale portion of the tonometer was read. That force, divided by the tonometer-eye contact area, gives the intraocular pressure. Thus the prior art devices rely in large part on the operator's judgment that the entire end of the tonometer is in contact with the eye; i.e., the point at which to stop further application of force against the eye and to take the force reading.

One such contact tonometer is disclosed in U.S. Pat. No. 3,070,997 to Papritz, (commonly referred to as the "Goldmann applanation tonometer"), wherein an applanating prism is pressed against the eye with gradually increasing force while the operator illuminates and views the applanated corneal zone through the prism base. A sodium fluorescein solution is applied to the eye for staining lacrimal fluid, so that the applanation zone becomes readily visible. The tonometer tip is viewed through one-half of a slit lamp bimicroscope, so that at the point of applanation, the operator can align two semicircles and then remove the tonometer tip from the eye to read the resulting pressure value analogue from a force applying knob. This represents a two-step process which must be done for each eye.

The Goldman applanation tonometer relies heavily on operator judgment. Measurement of the force and reading force off a diode weighted plunger put on the eye by a split screen image. The operator dials in a force until the image on the screen lines up a certain way. Also, sensitivity of the patient to fluorescein may be a problem if the test requires introduction of that foreign agent in the eye.

Pneumatic tonometers (known as pneumotonometers) generally include an air bearing piston having a pivoting probe tip to contact the corneal surface when urged forward by gas flowing to the probe tip beneath a thin membrane to emerge through small vents. Corneal pressure against the membrane causes a seal, but as gas pressure rises pushing the membrane against the eye with increasing force, pressure becomes sufficiently high to void the seal beneath the membrane. Gas escapes through the vents and pressure stabilizes at or very near intraocular pressure. However, such devices may be inaccurate at high IOP ranges; frequent maintenance is required; there is a requirement for use of an inert gas, such as freon and the gas cylinders must be replaced at regular intervals; and such devices may be problematic for the occurence of membrane leaks.

There is a need for an improved contact tonometer which would operate with a high degree of accuracy; obviate the need for fluoroscein and the use of any gas in intraocular pressure measurement; be manufactured by relatively simpler and less expensive production; simultaneously register the force applied and corneal area contacted in a single step process; reduce or eliminate the number of moving parts; and effectively diminish the potential variance of IOP measurements which may result from operator error variance due to moving parts.

SUMMARY OF THE INVENTION

It is a first object of the present invention, therefore, to provide a contact tonometer to register highly accurate intraocular measurements in a single-step process, while avoiding the application of fluorescein to the cornea and circumventing the use of any inert gas.

It is a second object of the present invention to provide a tonometer wherein the device itself indicates that point at which the tonometer-eye contact area is maximized, thereby reducing operator error.

Another object of the invention is to provide a tonometer which indicates the point at which a certain eye contact area is attained and simultaneously indicates pressure exerted on the cornea at that point.

Yet another object of this invention is to provide a tonometer of simplified design with reduced reliance on metallic springs or cams whose accuracy may be dependent on uniformity of their spring or cam systems; and, which may be made with consistancy in manufacture by relatively simpler, less expensive but uniform production of the tonometer.

Still another object of the invention is to provide a tonometer with no moving parts.

These and other objects of the invention are achieved by a device for the measurement of intraocular pressure, wherein a lightpipe is provided; and the cylinder has a circular sensorhead end creating a predefined or predetermined applanation area of corneal contact. A light source is positioned to direct light toward the sensorhead and area of corneal contact, such that the reflection of light from the corneal contact area increases as sensorhead-corneal contact area increases.

A photosensor then registers the reflected light to the maximum of the predetermined corneal contact area; and, a force sensor simultaneously registers and measures the force applied. Electronic circuitry is provided to be responsive to the outputs of the photosensor for measuring the point of maximum light reflection, i.e., the maximum measurable applanation area, simultaneously responsive to the force sensor.

Finally, electronic circuitry is provided and the circuitry, which may be a microprocessor, is simultaneously responsive to said force sensor and incorporates therein a means for determining intraocular pressure from said force and contact area measurements.

In this first embodiment, a black ring may be provided around the edge of the transparent cylinder to form a defined edge, the purpose of which is to obtain a specific area, such that when the pressure (force) is known, a force per area measurement can be made.

In a second embodiment of the invention, the device for measurement of intraocular pressure includes a cylindrical metallic sensor probe having a circular sensorhead for contacting the eye and creating an applanated area by corneal contact. Then an alternating current electrical source is provided which has a first grounded terminal and a second terminal leading to a series resistor which further connects the electrical source to the sensorhead.

A force sensor is provided along with an alternating current voltmeter with one input terminal grounded and the other input terminal connected to said sensorhead. The voltmeter output signal is inversely proportional to the corneal contact area. Electronic circuitry which may again be a microprocessor, is responsive to the output of the voltmeter. The electronic circuitry simultaneously responds to the voltmeter output and to the force sensor, and contains means for determining intraocular pressure from said force and contact area measurements.

In both embodiments of the invention, i.e, the device measuring maximum applanation area with a photosensor or the second embodiment with a voltmeter to measure capacitance or inductance, pressure is exerted on the eye to increase the size of the flattened area to a maximum predetermined value by increasing the force with which the surface at the outer end of the tonometer is pressed against the cornea.

This invention simplifies determining intraocular pressure (IOP) and control errors avoided when checking coverage of the probe on the flattened area. The reason is that in accordance with this invention the area of the flattened (applanated) surface is registered, and pressure is recorded, when light reflected from the corneal surface is maximized; i.e., where that maximum reflected light becomes constant; or, alternatively in the second embodiment, denoting the decreased voltage output signal and concomitant measurement of force pressure at that point.

By use of the device of the invention disclosed herein, either the first or second embodiment thereof, a process for measuring intraocular pressure may be practiced wherein such method comprises the steps of: contacting the eye with a cylindrical probe for exerting a force on the eye to create a defined corneal applanation area; registering a predetermined corneal applanation area by means of a maximum signal from an area sensing device; registering the force reading at the instant the maximum signal from the area sensor indicates the defined applanation area has been attained thereby measuring intraocular pressure.

BRIEF DESCRIPTION OF THE DRAWINGS

The present invention will be best understood when reference is made to the accompanying drawings which diagrammatically illustrate embodiments of the invention and the preferred embodiment thereof, and wherein identical part numbers are used to refer to identical parts and wherein:

FIGS. 1A, 1B, 1C and 1D are end views of the outer end of the probe indicating the predetermined maximum contact area, and demonstrating in sequence that with increased pressure on the surface of the eye, reflected light increases to that maximum contact area.

FIG. 2 graphically demonstrates the relationship of light sensor output to force sensor output, wherein increased force of the probe on the eye results in increased signal output, but only to a predetermined maximum contact area (point A), whereupon the signal flattens to a constant output.

DETAILED DESCRIPTION OF THE INVENTION

Figure 3:
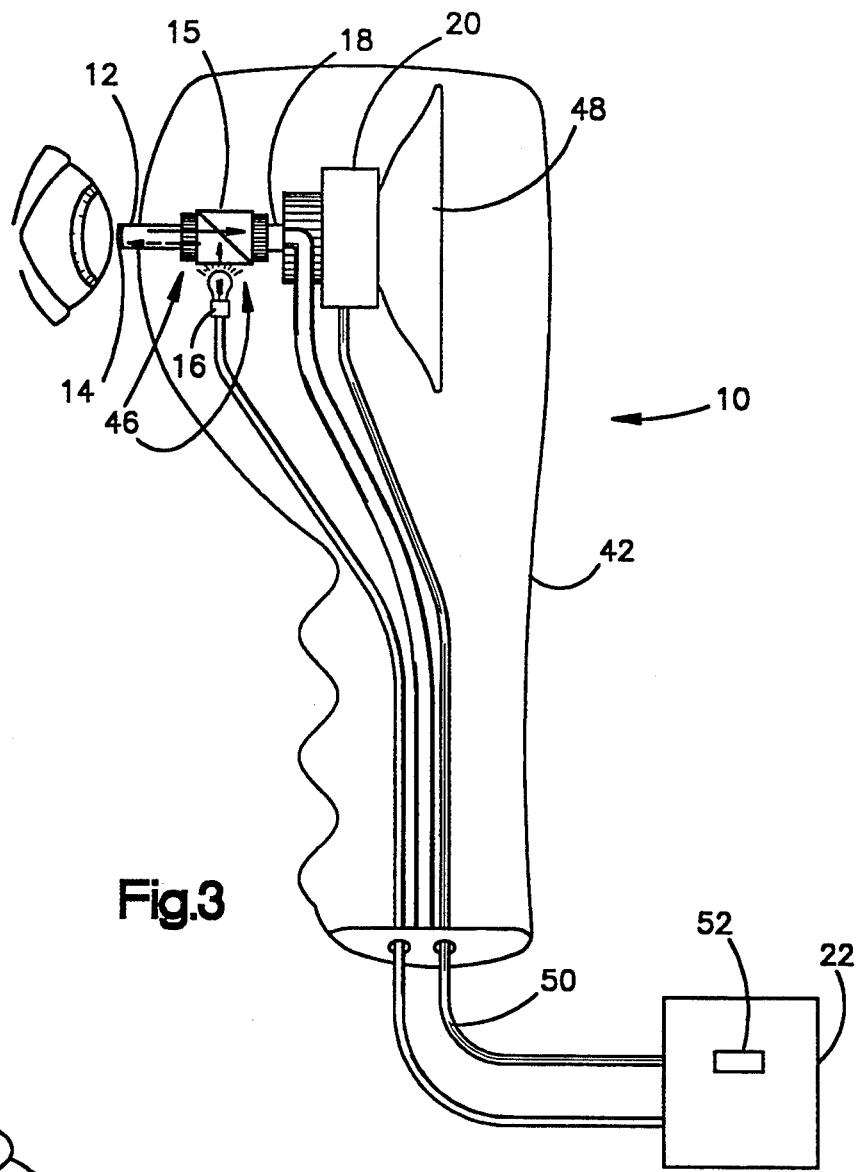
FIG. 3 is a plan view of the contact tonometer of the invention.

Applanation tonometers presently in use usually involve an operator placing the device on the cornea of the eye for the purpose of exerting some pressure against the eye. As the device is pressed onto the corneal surface, the area of contact with the eye increases as the force increases because the eye deforms under pressure of the pushing force. The pushing force in the contact area gives a pressure, which equals the pressure in the eye. This relationship exists because of the characteristics of the eye closely resembling a sack filled with an incompressible fluid.

The measurement cannot be made unless the contact area is known, so operators of prior art tonometers continue tonometer pressure onto the eye, either manually or mechanically until the entire end of the device contacts the eye. This involves subjective judgment on the part of the operator. When an operator determines that the end of the device completely contacts the eye, then the force scale is read. This force, divided by the area of the end of the contact point of the tonometer, gives intraocular pressure.

The present invention represents a significant improvement over devices used in the prior art for the reason that there are no moving parts, intraocular pressure is measured by a single step procedure, and the need for operator judgment is obviated.

Referring now to the drawings, FIG. 1A through 1D, an end view of the probe 12 having a sensorhead 14, indicates how the outer end 12A of the probe defines a predetermined maximum contact area 26, and that when the probe having a sensorhead at the outer end, initially contacts the corneal surface of the eye 100, some light is reflected from that surface.

Then as pressure is increased, the probe sensorhead-corneal surface contact area increases with direct resultant increase of reflected light 36. Drawing FIG. 1B and 1C demonstrate sequentially that the reflected light 36 is increased with increasing pressure of the tonometer 10 on the corneal surface of the eye 100. At some point, demonstrated by FIG. 1D, the sensorhead-corneal surface contact area is maximized to the point of the predetermined maximum contact area 26 and that is the crucial point for measurement of intraocular pressure or IOP.

The conversion of the degree, or amount, of probe-corneal surface contact area into a proportional electric signal necessitates that a force sensor 20 be associated with the sensorhead 14 of probe 12 having the predetermined maximum contact area 26 at its outer end 12A.

Reference to FIG. 3 indicates that in a first embodiment, the signal sensor is a photosensor 18 for receiving the reflected light 36 and the photosensor provides an electrical output proportional to the reflected light 36 received. The light source for the reflected light may be a bulb or a Light Emitting Diode or LED 16, whereby light is directed toward the corneal surface of the eye 100 by a beamsplitter 15. The light projects through a probe 12 preferably formed as a cylindrical lightpipe. The preferable configuration for the LED 16, beamsplitter 15, probe 12, photosensor 18 and force sensor 20 is shown by FIG. 3, wherein light from the LED 16 and reflected light are maximized since the LED, beamsplitter 15, probe and photosensor are retained in relative positions by optically clear glue 46, and fortified within the case with the force sensor 20 secured to the mounting case 44 portion of the body 40 by mounting plate 48.

As shown by the graph of FIG. 2, the signal received by the sensor and that sensor's resultant output increases as the force applied on the corneal surface increases, but only to the point of predetermined maximum contact area 36 of the probe, whereupon signal sensor output becomes constant. Stated in other words, when the contact area exceeds the predetermined maximum contact area 26, the signal output of the sensor does not increase further whereupon, at that crucial point, the output from the force sensor 20 associated with the sensorhead 14 of the probe must be determined, for this will give the intraocular pressure or IOP.

Thus having reached the predetermined maximum contact area point, if the pressure on the corneal surface increases, even though that pressure is increased, it would not result in a valid signal. A beep signal would indicate to the operator that the contact area signal has become constant. Although an audible alarm system may be used to indicate when the predetermined maximum contact area is reached, any suitable means may be used, such as a visual indicator or the like.

The light sensor or photosensor 18 is preferably a phototransistor or a photocell adapted to provide an electrical signal proportional to the light which output which is then be fed into an analog to digital (A/D) converter (not shown). The A/D converter interconnects with a microprocessor to read the photosensor's output and simultaneously, to read the force sensor output, whereupon the microprocessor program calculates and displays the intraocular pressure.

Alternatively in a second embodiment, the tonometer 10 of the present invention is operative by means of an electrical signal, i.e., a measure of capacitance or electrical impedance between a sensorhead 14 of the probe 12 and the corneal surface of the eye. As such, the sensorhead of the probe serves as one plate of a capacitor and in essence, the other capacitor plate is the surface of the eye itself. Since capacitance is proportional to the area, an alternating current signal is generated, and that signal having a medium to high frequency, and fed through a series resistor into one plate of the capacitor and then to ground.

A measure of voltage across the capacitor, since the upper resistor is a fixed value, as value of the capacitor increases, the voltage across it will decrease, whereupon that voltage can be converted into digital format with an A/D converter (not shown); that digital number can then be fed into a microprocessor 22, whereby at the lowest voltage point, representing the predetermined maximum corneal contact area point, pressure can be measured to give the intraocular pressure.

Figure 4:
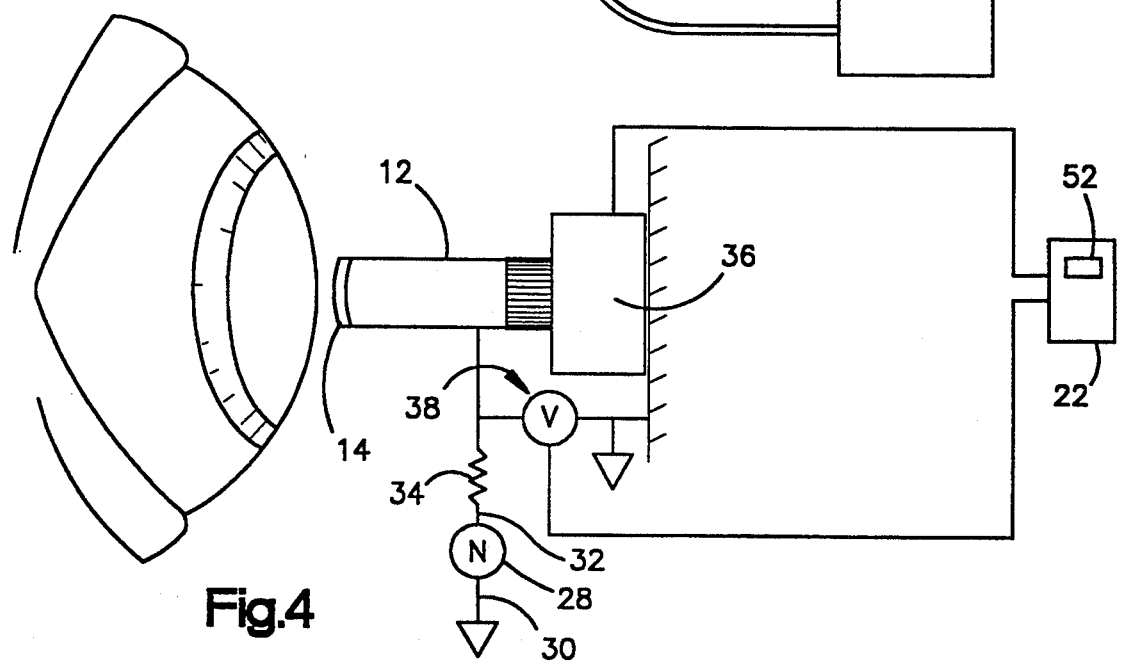
FIG. 4 is a schematic diagram for the second embodiment of the invention and indicates the electrical impedence circuit for signaling the predetermined maximum contact area.

Thus in the second embodiment, diagrammed in FIG. 4, the tonometer 10 of the present invention preferably has a lightweight body 40 forming an integral handle 42 and a mounting case 44, such that the tonometer 10 may be designed as a portable, hand-held device 10. A probe 12 is provided having an outer end 12A which projects from the body and an inner end 12B mounted within the case 44 portion of the body 40. The outer end 12A of the probe 12 includes a sensorhead 14 adapted for contacting and being pressed against the corneal surface of the eye 100 to provide a signal proportional to the pressure applied.

The probe 12 and sensorhead 14 are preferably constructed of an electrically conductive material. The sensorhead 14 is integral with the probe and forms the outer end of the probe; and the outer end 12A of the probe sensorhead has a predetermined maximum contact area 26. A back surface of force sensor 20 is mounted in the case 44, stabilized by attachment to a mounting plate 48. The front surface of force sensor 20 is mechanically attached to the inner end 12B of probe 12 and electrically insulated from probe 12.

An alternating current source (not shown) with frequency preferably in a range of 1 kilohertz to 10 megahertz, and the preferred voltage in a range of 1 millivolt to 1 volt, and having two terminals is provided. The first terminal 30 is grounded, while the second terminal 32 is preferably interconnected in series with a resistor 34 with the preferred resistance in a range between 10 megohms to 100 ohms.

There is further provided an alternating current voltmeter 38 which is also mounted in the case and electrically connected in parallel with the current source and probe. The voltmeter 38 is adapted to provide an electrical output inversely proportional to the probe-corneal surface contact area.

Electronic processing circuitry which is preferably a microprocessor 22, is interconnected with the outputs of both the force sensor 20 and voltmeter 38 and that circuitry or microprocessor includes the means for determining when said predetermined maximum corneal contact area is reached, and calculating means responsive to both the first output signal from the voltmeter and second output signal from the force sensor, for calculating the intraocular pressure per unit of contact area at that point of predetermined maximum corneal contact area. That microprocessor would also preferably be programmed to include a means for recording and means for indicating or displaying intraocular pressure per unit of contact area.

In the preferred embodiment, a beep signal would also be included for indicating to the operator that the contact signal has become constant; (in the case of reflected light—has stopped increasing; and in the case of electrical capacitance or impedance—has stopped decreasing).

When in use, the applanation tonometer 10 disclosed herein or either embodiment thereof, the outer end 12A of the probe having a sensorhead is placed and pressed against the corneal surface of the eye, with allowance of sufficient time for the contact area, and concomitant signal (light or electrical capacitance or impedance) emanating therefrom to reach a constant level. The predetermined corneal applanation area is reached when the signal stops varying and becomes constant; i.e., stops increasing in the case of the first embodiment wherein a first signal is generated by a light source and reflected light from the corneal surface of the eye; or stops decreasing in the case of the second embodiment wherein the first signal is generated by differential electrical capacitance or impedance between an electrically conductive outer end of the probe and corneal surface of the eye.

At that instant the force reading is determined and registered by electronic circuitry, preferably a microprocessor, whereupon the maximum signal level from the photosensor, or minimum signal from the voltmeter, indicates that the predefined applanation area has been attained thereby measuring intraocular pressure. That IOP can then be shown on the display 52 of the microprocessor 22.

A method of measuring intraocular pressure by means of the improved applanation tonometer disclosed herein includes the steps of providing the applanation tonometer having a body forming an integral handle portion and mounting case, a probe having inner and end mounted in said body and an outer end projecting therefrom and adapted to contact, and be pressed against a corneal surface of the eye; a sensorhead defining a predetermined maximum contact area at said outer end and a means for generating a first output signal proportional to the corneal contact area, said tonometer further having a force sensor associated with the sensorhead of the probe to monitor the intraocular pressure on the probe upon contact of said probe to the corneal surface of the eye and to provide a second output signal proportional to said pressure; a means for determining when said predetermined maximum contact area has been reached and a calculating means to calculate intraocular pressure at that point.

The step is then taken of pressing an outer end of the probe against the corneal surface of an eye. And the next sequential step is generating a first signal proportional to corneal surface area contacted by the probe to a sensor providing an output signal proportional to corneal surface area contacted by the probe.

In a next step, intraocular pressure is monitored upon contact of the probe against the corneal surface of an eye and then generating a second signal to a force sensor and an output signal proportional to pressure is provided.

An indicator generates a signal when the maximum corneal contact area has been reached by a means for determining that predetermined maximum contact area has been reached.

The intraocular pressure per unit of contact area is then calculated by the electronic processing circuitry when said maximum corneal contact area has been reached.

What is claimed is:

1. A method of measuring intraocular pressure comprising the steps of:

providing an applanation tonometer having a body forming an integral handle portion and mounting case, a probe having an inner end mounted in said body and an outer end projecting therefrom and adapted to contact, and be pressed against a corneal surface of the eye; a sensorhead defining a predetermined maximum contact area at said outer end and a means for generating a first output signal proportional to the corneal contact area; said tonometer further having a force sensor associated with the sensorhead of the probe to monitor the intraocular pressure on the probe upon contact of said probe to the corneal surface of the eye and to provide a second output signal proportional to said pressure; and electronic processing circuitry having a means for determining when said predetermined maximum contact area has been reached and a calculating means to calculate intraocular pressure at that point;

pressing said sensorhead at the outer end of said probe against the corneal surface of an eye;

generating a first signal proportional to corneal surface area contacted by the probe to a sensor providing an output signal proportional to said corneal contact area;

monitoring intraocular pressure upon contact of the probe against the corneal surface of an eye and generating a second signal to a force sensor and providing a second output signal proportional to pressure;

generating an indication of when said maximum corneal contact area has been reached by said means for determining said predetermined maximum contact area; and, calculating the intraocular pressure per unit of contact area by the calculating means of said electronic processing circuitry when said maximum corneal contact area has been reached.

2. An improved applanation tonometer for measurement of intraocular pressure of an eye, having a body forming an integral handle portion and mounting case, a probe having an inner end mounted in said body and an outer end projecting therefrom and adapted to contact, and be pressed against, a corneal surface of the eye, wherein the improvement comprises:
- said probe having a sensorhead defining a predetermined maximum corneal contact area at said outer end;
- a means for generating a first output signal proportional to the corneal contact area of said sensorhead; said means for generating the first output signal comprising an alternating current source having two terminals, a first grounded terminal and a second terminal interconnected in series with a resistor, and said resistor further connecting with said contact area of the probe, said probe constructed of an electrical conductive material; and an alternating current voltmeter mounted within the mounting case and positioned in parallel with said current source and said probe, said voltmeter adapted to provide an electrical output inversely proportional to the probe-corneal surface contact area;
- a force sensor associated with said sensorhead of the probe adapted to monitor the intraocular pressure on the probe upon contact of said probe to the corneal surface of the eye and to provide a second output signal proportional to said pressure; and,
- electronic processing circuitry interconnected with the outputs of, and simultaneously responsive to, both said voltmeter and said force sensor, said circuitry having a means for determining when said maximum contact area is reached based on said voltmeter output and calculating means simultaneously responsive to both said voltmeter and force sensor output signals to calculate intraocular pressure per unit of contact area at that point of predetermined maximum corneal contact area.

3. The applanation tonometer described in claim 2, wherein the electronic processing circuitry has as inputs thereto said first and second output signals from the voltmeter and said force sensor, and wherein said means for determining and said calculating means is a microprocessor programmed to receive the electrical outputs from said voltmeter and said force sensor and to automatically determine said maximum contact area and calculate intraocular pressure at that point.

4. The applanation tonometer described in claim 2, wherein the force sensor comprises a load cell.

5. An improved applanation tonometer for measurement of intraocular pressure of an eye, having a body forming an integral handle portion and mounting case, a probe having an inner end mounted in said body and an outer end projecting therefrom and adapted to contact, and be pressed against, a corneal surface of the eye, wherein the improvement comprises:
- said probe having a sensorhead defining a predetermined maximum corneal contact area at said outer end and a means for generating a first output signal proportional to the corneal contact area of said sensorhead; wherein the means for generating said first signal proportional to a corneal area contacted by the sensorhead of said probe comprises a light source positioned in said mounting case to direct light toward the contact area between the outer end of the probe and the corneal surface, and said light reflected from the corneal surface back toward the inner end of said probe to a photosensor, said photosensor mounted in said tonometer body to receive reflected light from said corneal surface, to transform reflected light to an electrical output and to generate said first output signal proportional to the reflected light; said reflected light being directly proportional to the corneal area contacted by the probe and increasing up to said predetermined maximum contact area of the probe;
- a force sensor associated with said sensorhead of the probe adapted to monitor the intraocular pressure on the probe upon contact of said probe to the corneal surface of the eye and to provide a second output signal proportional of said pressure;
- electronic processing circuitry having as inputs thereto said first and second output signals and means for determining when said predetermined maximum contact area is reached based upon said first signal and calculating means which is simultaneously responsive to both said first and second output signals to calculate said intraocular pressure per unit of contact area at that point of maximum corneal contact area.

6. The applanation tonometer described in claim 5, wherein the light source is a bulb positioned in said mounting case near the inner end of said probe.

7. The applanation tonometer described in claim 5, wherein the light source is a light emitting diode positioned in said mounting case near the inner end of said probe.

8. The applanation tonometer described in claim 5, wherein:
- said probe is constructed as a glass rod forming a lightpipe, with said outer end of the probe constructed of an optically transmissive material.

9. The applanation tonometer described in claim 5, wherein the electronic processing circuitry is a microprocessor which receives said first and second signals from said photosensor and the force sensor respectively and automatically calculates and indicates intraocular pressure at the point of maximum reflected light from said predetermined maximum contact area of said sensorhead of the probe.

10. The applanation tonometer described in claim 5, wherein the force sensor comprises a load cell.

11. The applanation tonometer described in claim 5, wherein the means for generating a first electrical signal, comprises:
- an alternating current source having two terminals, a first grounded terminal and a second terminal interconnected in series with a resistor, and said resistor further connecting with said contact area of the probe, said probe constructed of an electrical conductive material;
- an alternating current voltmeter mounted within the mounting case and positioned in parallel with said current source and said probe, said voltmeter adapted to provide an electrical output inversely proportional to the probe-corneal surface contact area; and,
- electronic processing circuitry interconnected with the outputs of, and simultaneously responsive to, both said voltmeter and said force sensor, said circuitry having a means for determining when said maximum contact area is reached based on said voltmeter output and calculating means simultaneously responsive to both said voltmeter and force sensor output signals to calculate intraocular pressure per unit of contact area at that point of predetermined maximum corneal contact area.

* * * * *